United States Patent
Li

(10) Patent No.: US 12,281,361 B2
(45) Date of Patent: Apr. 22, 2025

(54) METHYLATION MODIFICATION-BASED TUMOR MARKER STAMP-EP2

(71) Applicant: SHANGHAI EPIPROBE BIOTECHNOLOGY CO., LTD., Shanghai (CN)

(72) Inventor: Zhenyan Li, Shanghai (CN)

(73) Assignee: SHANGHAI EPIPROBE BIOTECHNOLOGY CO., LTD., Shanghai (CN)

(*) Notice: Subject to any disclaimer, the term of this patent is extended or adjusted under 35 U.S.C. 154(b) by 1034 days.

(21) Appl. No.: 17/250,458

(22) PCT Filed: Jul. 19, 2019

(86) PCT No.: PCT/CN2019/096797
§ 371 (c)(1),
(2) Date: May 19, 2021

(87) PCT Pub. No.: WO2020/020072
PCT Pub. Date: Jan. 30, 2020

(65) Prior Publication Data
US 2021/0292850 A1  Sep. 23, 2021

(30) Foreign Application Priority Data
Jul. 26, 2018 (CN) .......................... 201810830855.5

(51) Int. Cl.
*C12Q 1/6886* (2018.01)
(52) U.S. Cl.
CPC ..... *C12Q 1/6886* (2013.01); *C12Q 2600/154* (2013.01)
(58) Field of Classification Search
CPC ............................................... C12Q 2600/154
See application file for complete search history.

(56) References Cited

U.S. PATENT DOCUMENTS

| 2007/0161031 A1 | 7/2007 | Trinklein et al. | |
| 2009/0264306 A1* | 10/2009 | Caldwell | C12Q 1/6886 435/6.12 |
| 2009/0305256 A1 | 12/2009 | Pfeifer et al. | |
| 2010/0279879 A1* | 11/2010 | Kamalakaran | C12Q 1/6886 506/7 |

FOREIGN PATENT DOCUMENTS

| CN | 101861398 A | 10/2010 |
| CN | 104046686 A | 9/2014 |
| CN | 108866191 A | 11/2018 |
| WO | WO-2007050706 A2 | 5/2007 |
| WO | WO-2007050706 A3 | 5/2007 |
| WO | WO-2008073303 A2 | 6/2008 |
| WO | WO-2008073303 A3 | 6/2008 |
| WO | WO-2020020072 A1 | 1/2020 |

OTHER PUBLICATIONS

Holmes et al. Performance evaluation of kits for bisulfite-conversion of DNA from tissues, cell lines, FFPE tissues, aspirates, lavages, effusions, plasma, serum, and urine. PLoS One. Apr. 3, 2014;9(4):e93933. doi: 10.1371/journal.pone.0093933. PMID: 24699908; PMCID: PMC3974851 (Year: 2014).*
GenBank: *Homo sapiens* chromosome 5, BAC clone 249h5 (LBNL H149), complete sequence ; Accession: AC005618.1, Sep. 5, 1998 (Year: 1998).*
Yang et al. ; Methylation profiling defines an extensive field defect in histologically normal prostate tissues associated with prostate cancer. Neoplasia. Apr. 2013;15(4):399-408. doi: 10.1593/neo. 13280. PMID: 23555185; PMCID: PMC3612912. (Year: 2013).*
GenBank: AC005618.1 (Year: 1998).*
Chuang, C-K., et al., "Hypermethylation of the CpG islands in the promoter region flanking GSTP1 gene is a potential plasma DNA biomarker for detecting prostate carcinoma," *Cancer Detection and Prevention* 31(1):59-63, Elsevier, Netherlands (Dec. 2007).
Genbank, "*Homo sapiens* protocadherin gamma cluster (PCDHG@) on chromosome 5," Accession No. NG_000012.2, accessed at https://www.ncbi.nlm.nih.gov/nuccore/NG_000012 on May 18, 2021, 24 pages (2001).
International Search Report and Written Opinion for International Application No. PCT/CN2019/096797, China National Intellectual Property Administration, China, mailed on Oct. 9, 2019, 21 pages (with English Translation).
Shan, M., et al., "Detection of aberrant methylation of a six-gene panel in serum DNA for diagnosis of breast cancer," *Oncotarget* 7(14):18485-18494, Impact Journals LLC, United States (Feb. 2016).
Yu, J., et al., "Screening of differential DNA methylation loci in colorectal cancer by gene microarray technique," *Chinese Journal of Gastroenterology* 23(6):330-335, Shanghai Institute of Digestive Diseases, China (Jun. 2018).
Miyamoto, K., et al., "Identification of 20 genes aberrantly methylated in human breast cancers," *Int. J. Cancer* 116(3):407-414, Wiley, United States (2005).
Powrozek, T., et al., "Analysis of RTEL1 and PCDHGB6 promoter methylation in circulating-free DNA of lung cancer patients using liquid biopsy: A pilot study," *Exp. Lung Res.* 42(6): 307-313, Informa, United Kingdom (2016).

(Continued)

*Primary Examiner* — Aaron A Priest
*Assistant Examiner* — Tian Yu
(74) *Attorney, Agent, or Firm* — Sterne, Kessler, Goldstein & Fox P.L.L.C.

(57) ABSTRACT

Provided is a methylated tumor marker STAMP-EP2 and uses thereof in preparing a tumor diagnostic reagen. The tumor marker STAMP-EP2 herein is hypermethylated in all tumor types, is hypomethylated in corresponding normal tissue, and has high sensitivity and specificity; primers for detecting STAMP-EP2 may be used to prepare a tumor diagnostic kit.

6 Claims, 5 Drawing Sheets
Specification includes a Sequence Listing.

(56) References Cited

OTHER PUBLICATIONS

Vincent, A., et al., "Genome-wide analysis of promoter methylation associated with gene expression profile in pancreatic adenocarcinoma," *Clin. Cancer Res.* 17(13):4341-4354, American Association for Cancer Research, United States (2011).

Wang, K.H., et al., "Global methylation silencing of clustered proto-cadherin genes in cervical cancer: serving as diagnostic markers comparable to HPV," *Cancer Med.* 4(1):43-55, Wiley, United States (2015).

* cited by examiner

METHYLATION MODIFICATION-BASED TUMOR MARKER STAMP-EP2

REFERENCE TO A SEQUENCE LISTING SUBMITTED ELECTRONICALLY VIA EFS-WEB

The content of the electronically submitted sequence listing in ASCII text file (Name: 4790_0020001_Seqlisting_ST25; Size: 8,231 bytes; and Date of Creation: May 18, 2021) is herein incorporated by reference in its entirety.

FIELD OF DISCLOSURE

The disclosure is in the field of disease diagnostic markers. More specifically, the disclosure relates to a methylation based tumor marker STAMP, Specific Tumor Aligned Methylation of Pan-cancer.

BACKGROUND OF DISCLOSURE

The occurrence and development of tumor is a complex, multi-level, multi-factor dynamic process, including the complex interaction of external environment, genetic variations and epigenetic changes, etc. Environmental factors include carcinogenic physical, chemical, biological and other factors as well as unhealthy living habits. Genetic variations include gene mutation, copy number variation, chromosome translocation and so on. Epigenetic changes mainly include DNA methylation, histone modification, non-coding RNA and other factors. In the process of tumor occurrence and development, environmental, genetic and epigenetic factors complement each other and act together, leading to a series of inactivation of tumor suppressor genes and activation of proto-oncogenes, thereby causing tumor. The three factors act throughout the development of tumor and interact with each other. However, in the occurrence and early stage of tumor, the three factors play each role in sequence. For human beings, there are still many challenges for tumor therapy at present. Although new surgical methods, targeted therapy and immunotherapy have made some gratifying progress in recent years, there are still many misconceptions about tumor. The major problems of tumor metastasis, recurrence, heterogeneity and drug resistance need to be solved urgently.

There are many types of tumors in human body, and the occurrences of tumors can be found in most of the tissues. Different types of tumors can be divided into many subtypes. Especially in recent years, the classification of tumors is more detailed due to the progress in tumor molecular biology. For different types, different stages or different molecular subtypes of tumors, the therapeutic regimes are also different.

With the deepening of the understanding in tumor and the progress of science and technology, many new tumor markers have been found and used in clinical diagnosis. Before 1980, tumor markers were mainly hormones, enzymes, proteins and other cell secretions, such as carcinoembryonic antigen (CEA) and alpha fetoprotein (AFP) used as markers of gastric cancer, liver cancer and other tumors, carbohydrate antigen 125 (CA125) used as a marker of cervical cancer, and prostate specific antigen (PSA) used as a marker of prostate cancer. Although these tumor markers are still used in clinic, their sensitivity and accuracy can not meet the clinical needs.

Fluid biopsy is a technique for the diagnosis and prediction of tumors using circulating tumor cells or circulating tumor DNA as detection targets. The technology is still in its infancy, having many shortcomings. First, the sensitivity and specificity are not good enough. The tumor itself is heterogeneous, including a variety of subtypes of cell populations. The proportion of tumor DNA in clinical samples, especially blood samples, is very low. The existing tumor markers are difficult to meet the sensitivity of clinical requirements, and it is easy to cause misdiagnosis. Second, one marker has good effect only for one or a few kinds of tumors. As the DNA in blood are very complex, the existing tumor markers cannot solve the complex problems of tumor source and metastasis. Because of these complexities, it is difficult for many DNA methylation tumor markers to have a unified standard in clinical application, which seriously affects the sensitivity and accuracy of the markers. Different types of human tumors have both characteristics and commonness. A common marker for different tumors is of great significance for tumor screening, diagnosis, treatment and efficacy evaluation.

Therefore, it is urgent to develop new tumor markers with general applicability, high accuracy and allowing easy judgment in tumor diagnosis.

SUMMARY OF DISCLOSURE

The object of the disclosure is to provide a method for detecting tumor based on abnormal hypermethylation of specific sites in tumor using DNA methylation modification as tumor marker.

The first aspect of the present disclosure provides an isolated polynucleotide, including: (a) a polynucleotide with a nucleotide sequence as shown in SEQ ID NO: 1; (b) (a) a polynucleotide with a nucleotide sequence as shown in SEQ ID NO: 2; (c) a fragment of the polynucleotide of (a)-(b), having at least one (such as 2-45, more specifically 3, 5, 10, 15, 20, 25, 30, 40) CpG site with modification; (d) a nucleic acid (such as the polynucleotide with a nucleotide sequence as shown in SEQ ID No: 5 or 6) complementary to the polynucleotide or fragment of (a)-(c).

In a preferable embodiment, said modification includes 5-methylation, 5-hydroxymethylation, 5-formylcytosine (5fC) or 5-carboxylcytosine(5-caC).

The second aspect of the disclosure provides an isolated polynucleotide, which is converted from the polynucleotide of the first aspect, and as compared with the sequence of the first aspect, the cytosine C of the CpG site(s) with modification is unchanged, and the unmodified cytosine is converted into T or U.

In a preferable embodiment, it is converted from the polynucleotide corresponding to the first aspect by bisulfite treatment. In another preferable embodiment, the polynucleotide includes: (e) a polynucleotide with a nucleotide sequence as shown in SEQ ID NO: 3 or 7; (f) a polynucleotide with a nucleotide sequence as shown in SEQ ID NO: 4 or 8; (g) a fragment of the polynucleotide of (e)-(f), having at least one (such as 2-45, more specifically 3, 5, 10, 15, 20, 25, 30, 40) CpG site with modification.

The third aspect of the disclosure provides a use of the polynucleotide described in the first or second aspect in manufacture of a tumor detection agent or kit.

In a preferable embodiment, the tumors include (but are not limited to): hematologic cancers such as leukemia, lymphoma, multiple myeloma; digestive system tumors such as esophageal cancer, gastric cancer, colorectal cancer, liver cancer, pancreatic cancer, bile duct and gallbladder cancer; respiratory system tumors such as lung cancer, pleuroma; nervous system tumors such as glioma, neuroblastoma, meningioma; head and neck tumors such as oral cancer, tongue cancer, laryngeal cancer, nasopharyngeal cancer; gynecological and reproductive system tumors such as breast cancer, ovarian cancer, cervical cancer, vulvar cancer, testicular cancer, prostate cancer, penile cancer; urinary system tumors such as kidney cancer, bladder cancer, skin and other systems tumors such as skin cancer, melanoma, osteosarcoma, liposarcoma, thyroid cancer.

In another preferable embodiment, samples of the tumor include: tissue samples, paraffin embedded samples, blood samples, pleural effusion samples, and alveolar lavage fluid samples, ascites and lavage fluid samples, bile samples, stool samples, urine samples, saliva samples, sputum samples, cerebrospinal fluid samples, cell smear samples, cervical scraping or brushing samples, tissue and cell biopsy samples.

The fourth aspect of the disclosure provides a method of preparing a tumor detection agent, including: providing the polynucleotide described in the first or second aspect, designing a detection agent for specifically detecting the modification on CPG site(s) of a target sequence which is the full length or fragment of the polynucleotide; wherein, the target sequence has at least one (such as 2-45, more specifically, 3, 5, 10, 15, 20, 25, 30, 40) modified CpG site; preferably, the detection agent includes (but is not limited to) primers or probes.

The fifth aspect of the disclosure provides an agent or a combination of agents which specifically detect the modification on CPG site(s) of a target sequence, which is the full length or fragment of any of the polynucleotides described in the first or second aspect and has at least one (such as 2-45, more specifically, 3, 5, 10, 15, 20, 25, 30, 40) modified CpG site.

In a preferable embodiment, the agent or combination of agents is for a gene sequence containing the target sequence (designed based on the gene sequence), and the gene sequence includes gene Panels or gene groups.

In another preferable embodiment, the detection agent comprises: primers or probes.

In another preferable embodiment, the primers are: the primers shown in SEQ ID NO: 5 and 6.

In the sixth aspect of the disclosure, a use of the agent or combination of agents described in the fifth aspect of the disclosure in the manufacture of a kit for detecting tumors is provided; preferably, the tumors include (but are not limited to): digestive system tumors such as esophageal cancer, gastric cancer, colorectal cancer, liver cancer, pancreatic cancer, bile duct and gallbladder cancer; respiratory system tumors such as lung cancer, pleuroma; hematologic cancers such as leukemia, lymphoma, multiple myeloma; gynecological and reproductive system tumors such as breast cancer, ovarian cancer, cervical cancer, vulvar cancer, testicular cancer, prostate cancer, penile cancer; nervous system tumors such as glioma, neuroblastoma, meningioma; head and neck tumors such as oral cancer, tongue cancer, laryngeal cancer, nasopharyngeal cancer; urinary system tumors such as kidney cancer, bladder cancer, skin and other systems tumors such as skin cancer, melanoma, osteosarcoma, liposarcoma, thyroid cancer.

The seventh aspect of the present disclosure provides a detection kit, comprising container(s) and the agent or combination of agents described above in the container(s); preferably, each agent is placed in an independent container.

In another preferable embodiment, the kit also includes: bisulfite, DNA purification agent, DNA extraction agent, PCR amplification agent and/or instruction for use (indicating operation steps of the detection and a result judgment standard).

In the eighth aspect of the disclosure, a method for detecting the methylation profile of a sample in vitro is provided, including: (i) providing the sample and extracting the nucleic acid; (ii) detecting the modification on CPG site(s) of a target sequence in the nucleic acid of (i), wherein the target sequence is the polynucleotide described in the first aspect or the polynucleotide converted therefrom, which described in the second aspect.

In a preferable embodiment, in step (3), the analysis methods include pyrosequencing, bisulfite conversion sequencing, method using methylation chip, qPCR, digital PCR, second generation sequencing, third generation sequencing, whole genome methylation sequencing, DNA enrichment detection, simplified bisulfite sequencing technology, HPLC, MassArray, methylation specific PCR, or their combination, as well as in vitro detection and in vivo tracer detection for the combined gene group of partial or all of the methylation sites in the sequence shown in SEQ ID NO: 1. In addition, other methylation detection methods and newly developed methylation detection methods in the future can be applied to the disclosure.

In another preferable embodiment, step (ii) includes: (1) treating the product of (i) to convert the unmodified cytosine into uracil; preferably, the modification includes 5-methylation, 5-hydroxymethylation, 5-formylcytosine(5fC) or 5-carboxylcytosine(5-caC); preferably, treating the nucleic acid of step (i) with bisulfite; and (2) analyzing the modification on CPG site(s) of the target sequence in the nucleic acid treated by (1).

In another preferable embodiment, the abnormal methylation profile is the high level of methylation of C in CPG(s) of the polynucleotide.

In another preferable embodiment, the methylation profile detecting method is not for the purpose of directly obtaining the diagnosis result of a disease, or is not a diagnostic method.

The ninth aspect of the disclosure provides a tumor diagnosis kit, including primer pairs designed based on the sequence described in the first or second aspect of the disclosure, and gene Panels or gene groups containing the sequence, to obtain the characteristics of normal cells and tumor cells through DNA methylation detection.

Other aspects of the disclosure will be apparent to those skilled in the art based on the disclosure herein.

DETAILED DESCRIPTION

Figure 1:
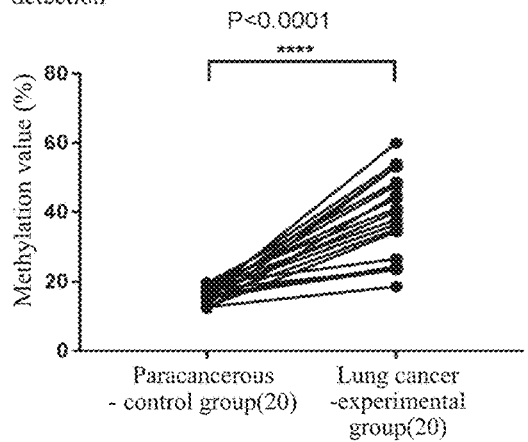
FIG. 1 shows comparison of STAMP-EP2 methylation value (left), the detection specificity and sensitivity (right) between control group and experimental group of 20 pairs of paracancerous-lung cancer samples, with paracancerous samples as control group, and lung cancer samples as experimental group.
Figure 1:
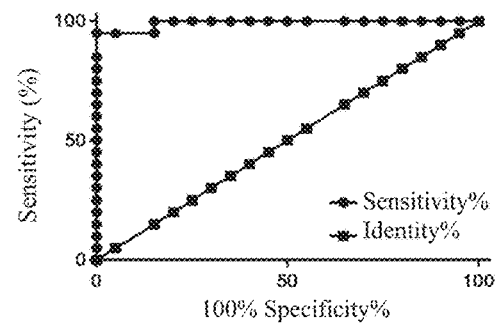

The inventor is committed to the research of tumor markers. After extensive research and screening, the inventor provides a universal DNA methylation tumor marker, STAMP (Specific Tumor Aligned Methylation of Pan-cancer). In normal tissues, STAMP was hypomethylated, while in tumor tissues, it was hypermethylated. It can be used for clinical tumor detection and as the basis of designing tumor diagnostic agents.

Term

As used herein, "isolated" refers to a material separated from its original environment (if the material is a natural material, the original environment is the natural environment). For example, in living cells, polynucleotides and polypeptides in their natural state are not isolated or purified, but the same polynucleotides or polypeptides will be isolated ones if they are separated from other substances existed in the natural state.

As used herein, "sample" includes substances suitable for DNA methylation detection obtained from any individual or isolated tissue, cell or body fluid (such as plasma).

As used herein, "hypermethylation" refers to high level of methylation, hydroxymethylation, 5-formylcytosine(5fC) or 5-carboxylcytosine(5-caC) of CpG in a gene sequence. For example, in the case of methylation specific PCR (MSP), if the PCR reaction with methylation specific primers has positive PCR results, the DNA (gene) region of interest is in hypermethylation state. For another example, in the case of real-time quantitative methylation specific PCR, hypermethylation can be determined based on statistic difference of the methylation status value as compared with the control sample.

As used herein, the tumors include but are not limited to: hematologic cancers such as leukemia, lymphoma, multiple myeloma; digestive system tumors such as esophageal cancer, gastric cancer, colorectal cancer, liver cancer, pancreatic cancer, bile duct and gallbladder cancer; respiratory system tumors such as lung cancer, pleuroma; nervous system tumors such as glioma, neuroblastoma, meningioma; head and neck tumors such as oral cancer, tongue cancer, laryngeal cancer, nasopharyngeal cancer; gynecological and reproductive system tumors such as breast cancer, ovarian cancer, cervical cancer, vulvar cancer, testicular cancer, prostate cancer, penile cancer; urinary system tumors such as kidney cancer, bladder cancer, skin and other systems tumors such as skin cancer, melanoma, osteosarcoma, liposarcoma, thyroid cancer.

Gene Marker

In order to find a useful target for tumor diagnosis, the inventor has identified the target of STAMP-EP2 after extensive and in-depth research. The methylation status with a nucleotide sequence as of STAMP-EP2 gene is significantly different between tumor tissues and non-tumor tissues. If abnormal methylation (hypermethylation) is detected in the promoter region of one of the above genes, the subject can be identified as having a high-risk of tumor. Moreover, the significant difference of STAMP-EP2 between tumor and non-tumor tissues exists in various types of tumors, including solid tumors and non-solid tumors.

Therefore, the disclosure provides an isolated polynucleotide from human genome, comprising the nucleotide sequence shown in the sequence of SEQ ID NO: 1, SEQ ID NO: 2, SEQ ID NO: 5 (the reverse complementary sequence of SEQ ID NO: 1), or SEQ ID NO: 6 (the reverse complementary sequence of SEQ ID NO: 2). For tumor cells of a cancer patient, the polynucleotide contains 5-methylcytosine (5mC) at C positions of many 5'-CpG-3'. The disclosure also comprises fragments of the polynucleotide of the sequence shown in SEQ ID NO: 1, 2, 5 or 6, having at least one (such as 2-45, more specifically 3, 5, 10, 15, 20, 25, 30, 40) methylated CpG site. The above polynucleotides or fragments can also be used in the design of detection agents or detection kits.

In some specific embodiments of the disclosure, the fragments of the polynucleotide are, for example, a fragment containing the residues 247-305 of SEQ ID NO: 1 (containing CpG sites 17-27 of SEQ ID NO: 1); a fragment containing the residues 249-307 of SEQ ID NO: 2 (containing CpG sites 18-28 of SEQ ID NO: 2). Antisense chains of the above fragments are suitable for use in the disclosure. Meanwhile, these fragments are merely examples of preferable embodiments of the present disclosure. Based on the information provided by the present disclosure, other fragments can also be selected.

In addition, gene Panels or gene groups containing the sequence shown in the SEQ ID NO: 1, 2, 5 or 6, or fragments thereof are also encompassed by the disclosure. For the gene Panel or gene group, the characteristics of normal cells and tumor cells can also be identified through DNA methylation detection.

The above polynucleotides can be used as the key regions for analysis of the methylation status in the genome. Their methylation status can be analyzed by various technologies known in the art. Any technique that can be used to analyze the methylation state can be applied to the present disclosure.

When treated with bisulfite, un-methylated cytosine(s) of the above polynucleotides will be converted into uracil, while methylated cytosine(s) remained unchanged.

Therefore, the disclosure also provides the polynucleotides obtained from the above polynucleotides after being treated with bisulfite, including the polynucleotides with a nucleotide sequence as shown in SEQ ID NO: 3, 4, 7 or 8. These polynucleotides can also be used in the design of detection agents or detection kits.

The disclosure also comprises fragments of the polynucleotides obtained from the above polynucleotides or the antisense chain thereof after being treated with bisulfite, wherein the fragments contain at least one methylated CpG site.

Detection Agents and Kits

Based on the new discovery of the disclosure, a detection agent designed based on said polynucleotide(s) is also provided for detecting the methylation profile of polynucleotide(s) in the sample in vitro. The detection methods and agents known in the art for determining the sequence and methylation of the genome can be applied in the disclosure.

Therefore, the disclosure provides a method of preparing a tumor detection agent, including: providing the polynucleotide, designing a detection agent for specifically detecting a target sequence which is the full length or fragment of the polynucleotide; wherein, the target sequence has at least one methylated CpG site.

The detection agent herein includes but is not limited to: primers, probes, etc.

For example, the agent is primer pairs. Based on the sequence of the polynucleotide, those skilled in the art know how to design primer(s). The two primers are on each side of the specific sequence of the target gene to be amplified (including CpG sequence, for the gene region originally methylated, the primer is complementary with CpG, and for the gene region originally un-methylated, the primer is complementary with TpG). It should be understood that based on the new discovery of the disclosure, those skilled in the art can design a variety of primers or probes or other types of detection agents for CpG sites at different positions on the target sequence or their combinations. These primers or probes or other types of detection agents should be included in the technical solution of the present disclosure.

The agent can also be a combination of agents (primer combination), including more than one set of primers, so that the multiple polynucleotides can be amplified respectively.

The disclosure also provides a kit for detecting the methylation profile of polynucleotide in a sample in vitro, which comprises container(s) and the above primer pair(s) in the container(s).

In addition, the kit can also include various reagents required for DNA extraction, DNA purification, PCR amplification, etc.

In addition, the kit can also include an instruction for use, which indicates operation steps of the detection and a result judgment standard, for the application of those skilled in the art.

Detection Method

The methylation profile of a polynucleotide can be determined by any technique in the art (such as methylation specific PCR (MSP) or real-time quantitative methylation specific PCR, Methylight), or other techniques that are still developing and will be developed.

Quantitative methylation specific PCR (QMSP) can also be used to detect methylation level. It is a continuous optical monitoring method based on fluorescent PCR, which is more sensitive than MSP. It has high throughput and avoids electrophoresis based result analysis.

Other available technologies include conventional methods in the art such as pyrosequencing, bisulfite conversation sequencing, qPCR, second generation sequencing, whole genome methylation sequencing, DNA enrichment detection, simplified bisulfite sequencing or HPLC, and combined gene group detection. It should be understood that, on the basis of the new disclosure herein, these well-known technologies and some technologies to be developed in the art can be applied to the present disclosure.

As a preferable embodiment of the disclosure, a method of detecting the methylation profile of a polynucleotide in a sample in vitro is also provided. The method is based on the follow principle: the un-methylated cytosine can be converted into uracil by bisulfite, which can be transformed into thymine in the subsequent PCR amplification process, while the methylated cytosine remains unchanged; therefore, after the polynucleotide is treated by bisulfite, the methylated site presents a polynucleotide polymorphism (SNP) similar to C/T. Based on the above principle, methylated and un-methylated cytosine can be distinguished effectively by identifying the methylation profile of a polynucleotide in the sample.

The method of the disclosure includes: (a) providing samples and extracting genomic DNA; (b) treating the genomic DNA of step (a) with bisulfite, so as to convert the un-methylated cytosine in the genomic DNA into uracil; (c) analyzing whether the genomic DNA treated in step (b) contains an abnormal methylation profile.

The method of the disclosure can be used for: (i) analyzing whether a subject has tumor by detecting the sample of the subject; (ii) identifying a population having high-risk of tumor. The method needs not to be aimed at obtaining direct diagnosis results.

In a preferable embodiment of the disclosure, DNA methylation is detected by PCR amplification and pyrosequencing. It should be understood by those in the art that DNA methylation detection is not limited to these methods, and any other DNA methylation detection method can also be used. The primers used in PCR amplification are not limited to those provided in Examples.

Because of bisulfite treatment, in which un-methylated cytosine in genomic DNA are converted into uracil and then transformed into thymine in the subsequent PCR process, the sequence complexity of the genome will be reduced, and it will be more difficult to amplify specific target fragments by PCR. Therefore, in order to improve amplification efficiency and specificity, nested PCR may be preferable, wherein two sets of primers (outer primers and inner primers) are used in two successive runs of PCR, and the amplification product from the first run undergoes a second run with the second set of primers. However, it should be understood that the detection methods suitable for the present disclosure are not limited thereto.

After the research and verification on clinical samples, the method of the disclosure provides very high accuracy in the clinical diagnosis of tumors. The disclosure can be applied to the fields of tumor auxiliary diagnosis, efficacy evaluation, prognosis monitoring, etc., thus has a high clinical value.

The disclosure is further illustrated by the specific examples described below. It should be understood that these examples are merely illustrative, and do not limit the scope of the present disclosure. The experimental methods without specifying the specific conditions in the following examples generally used the conventional conditions, such as those described in J. Sambrook, Molecular Cloning: A Laboratory Manual (3rd ed. Science Press, 2002) or followed the manufacturer's recommendation.

Example 1. Nucleic Acid Sequence for STAMP-EP2 Detection

The sequence of the STAMP-EP2 tumor marker is provided as follows: SEQ ID NO: 1 (chr14: 140797163~140797701 (hg19/Human)), in which the underlined bases are methylated CpG sites, and each number below the underline indicates the site number.

```
1~50bp      CGCCGCCGTC GGCCAGTGCA GAGCAAGCGC TGACGCCGGG GATCCCTCAG
            01 02 0304                          05       06 07

51~100bp    CCTCTAGCCT GGGATTCCCT GCGCAGCCAA CAACAGAAAA GAAAACCAGC
                                  08

101~151bp   TCCCACACAG AGGCTCCCGG CTGCGCAGAC CTTGCCCAGC ACACCAGATT
                                  09   10

151~200bp   GCCAGCTCCG AGACCCGGGA CTCCTCCTGT CCTGGGCCGA ATGCTCTTTT
                     11        12                    13

201~251bp   AGCGCGGTAG AGTGCACTTT CTCCAACTGG AAAAGCGGGG ACCCAGCGAG
               14 15                                          17

251~300bp   AACCCGAGCG AACGATGGGA GGGAGCTGCG CGCAGAGGCG CCGGGCCGGC
               18 19    20                21 22      23 24  25

301~350bp   CCGCGGCAGG    TACTATTTCC TTTGCTGCTG CCTTTGTTCT ACCCCACGCT
               26 27                                              28

351~400bp   GTGTGAGCCG ATCCGCTACT CGATTCCGGA GGAGCTGGCC AAGGGCTCGG
                    29        30       31 32                    33

401~450bp   TGGTGGGGAA CCTCGCTAAG GATCTAGGGC TTAGTGTCCT GGATGTGTCG
                            34                                35
```

```
451~500bp GCTCGCGAGC TGCGAGTGAG CGCGGAGAAG CTGCACTTCA GCGTAGACGC
              ‾‾ ‾‾       ‾‾        ‾‾ ‾‾                 ‾‾    ‾‾
              36 37       38        39 40                 41    42 43

501~539bp GCAGAGCGGG GACTTACTTG TGAAGGACCG AATAGACCG
          ‾‾    ‾‾                     ‾‾        ‾‾
                44                     45        46
```

The bisulfite treated sequence from the above sequence is shown in SEQ ID NO: 3 (Y represents C or U) as follows:

```
1~50bp    YGUYGUYGTY GGUUAGTGUA GAGUAAGYGU TGAYGUYGGG GAUUUUUAG
          ‾‾ ‾‾ ‾‾                     ‾‾     ‾‾ ‾‾
          01 02 03 04                  05     06 07

51~100bp  UUTUTAGUUT GGGATTUUUT GYGUAGUUAA UAAUAGAAAA GAAAAUUAGU
                                ‾‾
                                08

101~151bp TUUUAUAUAG AGGUTUUYGG UTGYGUAGAU UTTGUUUAGU AUAUUAGAUU
                          ‾‾      ‾‾
                          09      10

151~200bp GUUAGUTUYG AGAUUYGGGA UTUUTUUTGT UUTGGGUYGA ATGUTUTTTT
              ‾‾        ‾‾                      ‾‾
              11        12                      13

201~251bp                                                UYGGGUYGGU
          AGYGYGGTAG AGTGUAUTTT UTUUAAUTGG AAAAGYGGGG    ‾‾   ‾‾
           ‾‾‾‾                                 ‾‾      24   25
          14 15                                 16

251~300bp AAUUYGAGYG AAYGATGGGA GGGAGUTGYG YGUAGAGGYG UYGGGUYGGU
              ‾‾ ‾‾    ‾‾           ‾‾       ‾‾  ‾‾   ‾‾   ‾‾
              18 19    20           21       22  23   24   25

301~350bp UYGYGGUAGG          TAUTATTTUU TTTGUTGUTG UUTTTGTTUT AUUUUAYGUT
          ‾‾ ‾‾                                                       ‾‾
          26 27                                                       28

351~400bp GTGTGAGUYG ATUYGUTAUT YGATTUYGGA GGAGUTGGUU AAGGGUTYGG
               ‾‾      ‾‾         ‾‾  ‾‾                   ‾‾
               29      30         31  32                   33

401~450bp TGGTGGGGAA UUTYGUTAAG GATUTAGGGU TTAGTGTUUT GGATGTGTYG
                        ‾‾                                    ‾‾
                        34                                    35

451~500bp GUTYGYGAGU TGYGAGTGAG YGYGGAGAAG UTGUAUTTUA GYGTAGAYGY
             ‾‾ ‾‾      ‾‾      ‾‾ ‾‾                 ‾‾    ‾‾
             36 67      38      39 40                 41    42 43

501~539bp GUAGAGYGGG GAUUUAUUUG TGAAGGAUYG AATAGAUYG
              ‾‾                      ‾‾        ‾‾
              44                      45        46
```

The sequence of the STAMP-EP2 tumor marker is provided as follows: SEQ ID NO: 2 (chr14: 140787504~140788044 (hg19/Human)), in which the underlined bases are methylated CpG sites, and each number below the underline indicates the site number;

```
1~50bp    CGCCGCTGTC GGCCAGTGCA GAGCAAGCGC TGACGCCGGG GATCCGTCAG
          ‾‾ ‾‾    ‾‾                 ‾‾    ‾‾ ‾‾         ‾‾
          01 02    03                 04    05 06         07

51~100bp  CCTCTGGCCT GGGATTCCCT GCGCAGCCAA CAACAGAAAG AAGAAAACCA
                                ‾‾
                                08

101~150bp GCTCCCACAC AGAGCCTCCC GGCTGCGCAG ACCTTTCCCA GCACAGCGGA
                           ‾‾        ‾‾                     ‾‾
                           09        10                     11

151~200bp TTGCCAGCTC CGAGACCCGG GACTCCTCCT GTCCTGGGCC GAATGCTCTT
                       ‾‾    ‾‾                  ‾‾
                       12    13                  14

201~250bp                                                 GGACCCAGCG
          TTAGCGCGGT AGAGTGCACT TTCTCCAACT GGAAAAGCGG           ‾‾
              ‾‾ ‾‾                             ‾‾              18
              15 16                             17

251~300bp AGAACCCGAG CGAACGATGG          CGCGCAGAGG CGCCGGGCCG
                ‾‾       ‾‾    GAGGGAGCTG ‾‾ ‾‾     ‾‾  ‾‾ ‾‾
                19       20 21           22 23     24  25 26

301~350bp GCCCGCGGCA          GGTGCTATTT CCTTTGCTGC TGCCTTTGTT CTACCCCACC
             ‾‾ ‾‾
             27 28

351~400bp CTGAGTGAGC CGATCCGCTA CTCGATTCCG GAGGAGCTGG CCAAGGGCTC
                        ‾‾ ‾‾        ‾‾ ‾‾                    ‾‾
                        29 30        31 32                    33
```

```
401~450bp GGTGGTGGGG AACCTCGCTA AGGATCTAGG GCTCAGTGTC CTGGATGTGT
                             34

451~500bp CGGCTCGCAA GCTGCGAGTG AGCGCGGAGA AGCTGCACTT CAGCGTAGAC
          35   36    37        38 39                 40      41

501~541bp GCGGAGAGCG GGGACTTACT TGTGAAGAAC CGAATAGACC G
          42      43                     44      45
```

The bisulfite treated sequence from the above sequence is shown in SEQ ID NO: 4 (Y represents C or U) as follows:

```
1~50bp     YGUYGUTGTY GGUUAGTGUA GAGUAAGYGU TGAYGUYGGG GATUYGTUAG
           01 02   03                    04   05 06         07

51~100bp   UUTUTGGUUT GGGATTUUUT GYGUAGUUAA UAAUAGAAAG AAGAAAAUUA
                                08

101~151bp  GUTUUUAUAU AGAGUUTUUY GGUTGYGUAG AUUTTUUUA GAUAGYGGA
                              09        10                 11

151~200bp  TTGUUAGUTU YGAGAUUYGG GAUTUUTUUT GTUUTGGGUY GAATGUTUTT
                      12      13                    14

201~251bp                                              GGAUUUAGYG
           TTAGYGYGGT AGAGTGUAUT TTUTUUAAUT GGAAAAGYGG          18
           15 16                                       17

251~300bp  AGAAUUYGAG YGAAYGATGG           YGYGUAGAGG YGUYGGGUYG
                   19     20 21  GAGGGAGUTG 22   23   24  25 26

301~350bp  GUUYGYGGUA GGTGUTATTT UUTTTGUTGU TGUUTTTGTT UTAUUUUAUU
                27 28

351~400bp  UTGAGTGAGU YGATUYGUTA UTYGATTUYG GAGGAGUTGG UUAAGGGUTY
                      29    30     31    32                    33

401~450bp  GGTGGTGGGG AAUUTYGUTA AGGATUTAGG GUTUAGTGTU UTGGATGTGT
                             34

451~500bp  YGGUTYGUAA GUTGYGAGTG AGYGYGGAGA AGUTGUAUTT UAGYGTAGAY
           35    36   37         38 39                40     41

501~541bp  GYGGAGAGYG GGGAUUTAUT TGTGAAGAAU YGAATAGAUY G
           42      43                      44      45
```

The reverse complementary sequence of SEQ ID NO: 1 is shown in SEQ ID NO: 5 as follows:

CGGTCTATTCGGTCCTTCACAAGTAAGTCCCCGCTCTGCGCGTCTACGC

TGAAGTGCAGCTTCTCCGCGCTCACTCGCAGCTCGCGAGCCGACACATC

CAGGACACTAAGCCCTAGATCCTTAGCGAGGTTCCCCACCACCGAGCCC

TTGGCCAGCTCCTCCGGAATCGAGTAGCGGATCGGCTCACACAGCGTGG

GGTAGAACAAAGGCAGCAGCAAAGGAAATAGTACCTGCCGCGGGCCGGC

CCGGCGCCTCTGCGCGCAGCTCCCTCCCATCGTTCGCTCGGGTTCTCGC

TGGGTCCCCGCTTTTCCAGTTGGAGAAAGTGCACTCTACCGCGCTAAAA

GAGCATTCGGCCCAGGACAGGAGGAGTCCCGGGTCTCGGAGCTGGCAAT

CTGGTGTGCTGGGCAAGGTCTGCGCAGCCGGGAGCCTCTGTGTGGGAGC

TGGTTTTCTTTTCTGTTGTTGGCTGCGCAGGGAATCCCAGGCTAGAGGC

TGAGGGATCCCCGGCGTCAGCGCTTGCTCTGCACTGGCCGACGGCGGCG

The reverse complementary sequence of SEQ ID NO: 2 is shown in SEQ ID NO: 6 as follows:

CGGTCTATTCGGTTCTTCACAAGTAAGTCCCCGCTCTCCGCGTCTACGC

TGAAGTGCAGCTTCTCCGCGCTCACTCGCAGCTTGCGAGCCGACACATC

CAGGACACTGAGCCCTAGATCCTTAGCGAGGTTCCCCACCACCGAGCCC

TTGGCCAGCTCCTCCGGAATCGAGTAGCGGATCGGCTCACTCAGGGTGG

GGTAGAACAAAGGCAGCAGCAAAGGAAATAGCACCTGCCGCGGGCCGGC

CCGGCGCCTCTGCGCGCAGCTCCCTCCCATCGTTCGCTCGGGTTCTCGC

TGGGTCCCCGCTTTTCCAGTTGGAGAAAGTGCACTCTACCGCGCTAAAA

GAGCATTCGGCCCAGGACAGGAGGAGTCCCGGGTCTCGGAGCTGGCAAT

CCGCTGTGCTGGGAAAGGTCTGCGCAGCCGGGAGGCTCTGTGTGGGAGC

TGGTTTTCTTCTTTCTGTTGTTGGCTGCGCAGGGAATCCCAGGCCAGAG

GCTGACGGATCCCCGGCGTCAGCGCTTGCTCTGCACTGGCCGACAGCGG

CG

The bisulfite treated sequence from SEQ ID NO: 5 is shown in SEQ ID NO: 7 (Y represents C or U) as follows:

YGGTUTATTYGGTUUTTUAUAAGTAAGTUUUYGUTUTGYGYGTUTAYGU

TGAAGTGUAGUTTUTUYGYGUTUAUTYGUAGUTYGYGAGUYGAUAUAUU

UAGGAUAUUAAGUUUUAGAUUUUAGYGAGGUUUUUUAUUAUYGAGUUU

TTGGUUAGUUUUTUYGGAAUYGAGUAGYGGAUYGGUUAUAUAGYGTGG

GGUAGAAUAAAGGUAGUAGUAAAGGAAAUAGUAUUUGUYGYGGGUYGGU

UYGGYGUUUTGTGYGYGUAGUUUUUUUUAUYGUUYGUUYGGGUUUUYGU

TGGGUUUUYGUTTTUUAGTTGGAGAAAGUGUAUUUAUYGYGUAAAA

GAGUAUUYGGUUUAGGAUAGGAGGAGUUUYGGGUUUYGGAGUUGGUAAU

UUGGUGUGUGGGUAAGGUUTGYGUAGUYGGGAGUUUUTGUGUGGGAGU

TGGUUUUUUUUUUUUGUUGUUGGUUGYGUAGGGAAUUUUAGGUUAGAGGU

TGAGGGAUUUUYGGYGUAGYGUUUGUUUGUAUUGGUYGAYGGYGGYG

The bisulfite treated sequence from SEQ ID NO: 6 is shown in SEQ ID NO: 8 (Y represents C or U) as follows:

YGGTUTATTYGGTUUTTUAUAAGTAAGTUUUYGUTUTUYGYGTUTAYGU

TGAAGTGUAGUTTUTUYGYGUTUAUTYGUAGUUYGYGAGUYGAUAUAUU

UAGGAUAUUGAGUUUUAGAUUUUAGYGAGGUUUUUUAUUAUYGAGUUU

TTGGUUAGUUUUTUYGGAAUYGAGUAGYGGAUYGGUUAUUUUAGGGUGG

GGUAGAAUAAAGGUAGUAGUAAAGGAAAUAGUAUUUGUYGYGGGUYGGU

UYGGYGUUUTGYGYGUAGUUUUUUUUAUYGUUYGUUUYGGGUUUUYGU

TGGGUUUUYGUTTTUUAGTTGGAGAAAGUGUAUUUAUYGYGUAAAA

GAGUAUUYGGUUUAGGAUAGGAGGAGUUUYGGGUUUYGGAGUUGGUAAU

UYGUGUGUGGGAAAGGUUTGYGUAGUYGGGAGGUUUTGUGUGGGAGU

TGGUUUUUUUUUUUUGUUGUUGGUUGYGUAGGGAAUUUUAGGUUAGAG

GUUGAYGGAUUUUYGGYGUAGYGUUUGUUUGUAUUGGUYGAUAGYGG

YG

Example 2. STAMP-EP2: Lung Cancer—Clinical Sample Assay—Pyrosequencing

1. Clinical samples: 20 pairs of paracancerous-lung cancer samples were obtained, with paracancerous samples as control group and 20 cases of lung cancer samples as experimental group;
2. DNA extraction: DNA was extracted from the experimental group and the control group respectively. Phenol-chloroform extraction method was used in this experiment, which is not limited thereto;
3. Bisulfite treatment: the extracted DNA samples were treated with bisulfite and the procedures were strictly followed. EZ DNA Methylation-Gold Kit (ZYMO Research, Cat #D5006) was used in this experiment, which is not limited thereto;
4. Primer design: PCR primers and pyrosequencing primers were designed according to the characteristics of SEQ ID NO: 1 and SEQ ID NO: 2 of STAMP-EP2 sequence. Due to the great similarity between SEQ ID NO: 1 and SEQ ID NO: 2, the primers designed in this experiment can simultaneously detect methylation of CpG sites 17, 18, 19, 20, 21, 22, 23, 24, 25, 26, and 27 of SEQ ID NO: 1 and CpG sites 18, 19, 20, 21, 22, 23, 24, 25, 26, 27 and 28 of SEQ ID NO: 2. Following PCR amplification, the methylation values of STAMP-EP2 were detected by pyrosequencing as the methylation values of CpG sites 17, 18, 19, 20, 21, 22, 23, 24, 25, 26, and 27 of SEQ ID NO: 1 and CpG sites 18, 19, 20, 21, 22, 23, 24, 25, 26, 27 and 28 of SEQ ID NO: 2. The PCR primers sequences, pyrosequencing primers sequences, the detecting sequences of pyrosequencing and the detected sites are shown in Table 1;

TABLE 1

| Primer Name | 5'-3' sequence | detected site |
|---|---|---|
| STAMP-EP2-Pyroseq-Primer-F | GAATGTTTTTTTAGY GYGGTAGAGTGTA (SEQ ID NO: 9) | CpG sites 17-27 of SEQ ID NO: 1 and |
| STAMP-EP2-Pyroseq-Primer-R(5'-Biotin modified) | CAACAACAAAAAAAA TAATACCTACC (SEQ ID NO: 10) | CpG sites 18-28 of SEQ ID NO: 2 |
| STAMP-EP2-Pyroseq-Primer-Seq | TTAATTGGAAAAGYG GGGATTTA (SEQ ID NO: 11) | |
| pyrosequencing detecting sequences | GYGAGAATTYGAGYG AAYGATGGGAGGGAG TTGYGYGTAGAGGYG TYGGGTYGGTTYGYG GT (SEQ ID NO: 12) | |

5. PCR amplification and agarose gel electrophoresis: The bisulfite treated samples were used as templates for PCR amplification. The specificity of PCR amplification was identified by agarose gel electrophoresis of the amplified products, and the size of the amplified fragment should be 143 bp;
6. Pyrosequencing: Pyro Mark Q96 ID pyrosequencing instrument (QIAGEN) was used for sequencing, and the procedures in instructions were strictly followed;
7. Calculation of STAMP-EP2 methylation value: pyrosequencing can detect the methylation values of CpG sites 17, 18, 19, 20, 21, 22, 23, 24, 25, 26, and 27 of SEQ ID NO: 1 and CpG sites 18, 19, 20, 21, 22, 23, 24, 25, 26, 27 and 28 of SEQ ID NO: 2 in the target region, and the average value were calculated as the STAMP-EP2 methylation value in the sample;
8. Results analysis: the methylation value of STAMP-EP2 was compared between the control group and the experimental group, as shown in FIG. 1. It shows that among the clinical samples of lung cancer, the STAMP-EP2 methylation value of the lung cancer experimental group was significantly increased, with P<0.0001, a sensitivity of 95% and a specificity of 100%.

Figure 2:
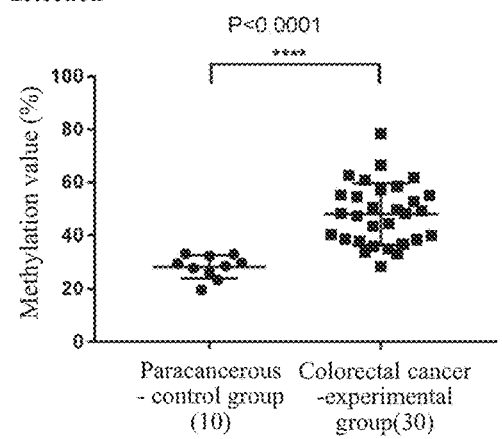
FIG. 2. 10 paracancerous clinical samples of colorectal cancer were used as the control group, and 30 colorectal cancer clinical samples were used as the experimental group. The STAMP-EP2 methylation value (left), the detection specificity and sensitivity (right) were compared between the control group and the experimental group.
Figure 2:
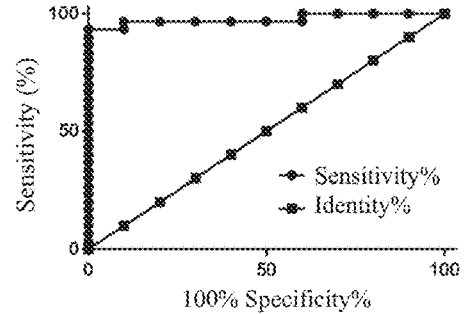

Example 2. STAMP-EP2: Colorectal Cancer—Clinical Sample Assay—Pyrosequencing 1. Clinical samples: 10 paracancerous clinical samples of colorectal cancer were used as the control group, and 30 colorectal cancer clinical samples were used as the experimental group;
2. Step 2, 3, 4, 5, 6, and 7 are the same as those in Example 2; 8. Results analysis: the methylation value of STAMP-EP2 was compared between the control group and the experimental group, as shown in FIG. 2. It showed that among the clinical samples of colorectal cancer, the STAMP-EP2 methylation value of the colorectal cancer experimental group was significantly increased, with P<0.0001, a sensitivity of 93.33% and a specificity of 100%.

Example 3. STAMP-EP2: Gastric Cancer—Clinical Sample Assay—Pyrosequencing

Figure 3:
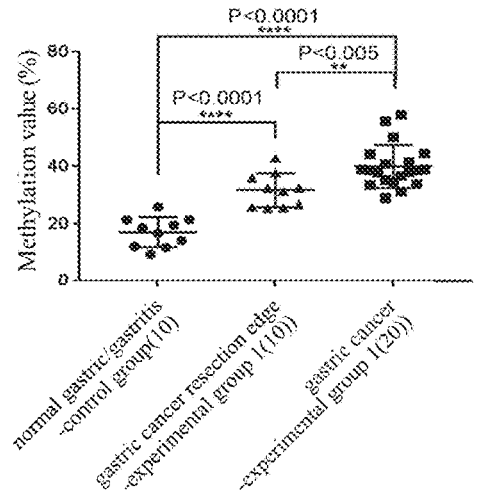
FIG. 3. 10 normal gastric (or gastritis) clinical samples were used as the control group, 10 gastric cancer resection edge clinical samples were used as the experimental group 1, and 20 gastric cancer clinical samples were used as experimental group 2. The STAMP-EP2 methylation value was compared among the three groups.

1. Clinical samples: 10 normal gastric (or gastritis) clinical samples were used as the control group, 10 gastric cancer resection edge clinical samples were used as the experimental group 1, and 20 gastric cancer clinical samples were used as experimental group 2;
2. Step 2, 3, 4, 5, 6, and 7 are the same as those in Example 2;
8. Results analysis: the methylation value of STAMP-EP2 was compared among the gastric (or gastritis) control group, the resection edge experimental group and gastric cancer experimental group 2, as shown in FIG. 3. The results showed that among the clinical samples of gastric cancer, the STAMP-EP2 methylation value of the gastric cancer experimental group 2 was significantly increased, P<0.0001. Meanwhile, the methylation of resection edge experimental group 1 was between the normal gastric (or gastritis) control group and the gastric cancer experimental group 2, which indicated that the methylation of STAMP-EP2 began to change at the resection edge. Therefore, as a marker of gastric cancer, STAMP-EP2 can be used to detect gastric cancer, and can also be used to determine the resection edge of gastric cancer.

Example 4. STAMP-EP2: Cervical Cancer—Clinical Sample Assay—Pyrosequencing

Figure 4:
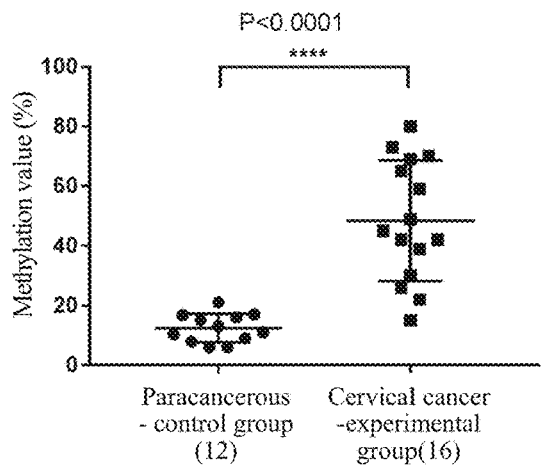
FIG. 4. 10 paracancerous clinical samples of colorectal cancer were used as the control group, and 30 colorectal cancer clinical samples were used as the experimental group. The STAMP-EP2 methylation value (left), the detection specificity and sensitivity (right) were compared between the control group and the experimental group.
Figure 4:
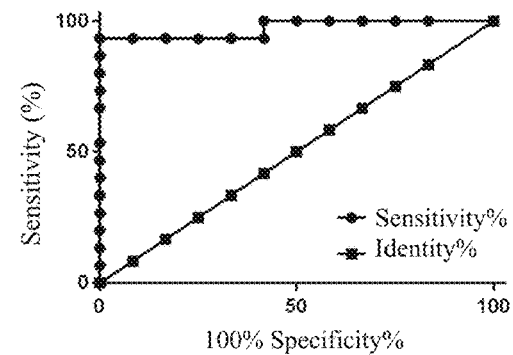

1. Clinical samples: 12 paracancerous clinical samples of cervical cancer were used as the control group, and 16 cervical cancer clinical samples were used as the experimental group;
2. Step 2, 3, 4, 5, 6, and 7 are the same as those in Example 2;
8. Results analysis: the methylation value of STAMP-EP2 was compared between the control group and the experimental group, as shown in FIG. 4. It shows that among the clinical samples of cervical cancer, the STAMP-EP2 methylation value of the cervical cancer experimental group was significantly increased, with P<0.0001, a sensitivity of 93.33% and a specificity of 100%.

Example 5. STAMP-EP2: Liver Cancer—Clinical Sample Assay—Pyrosequencing

Figure 5:
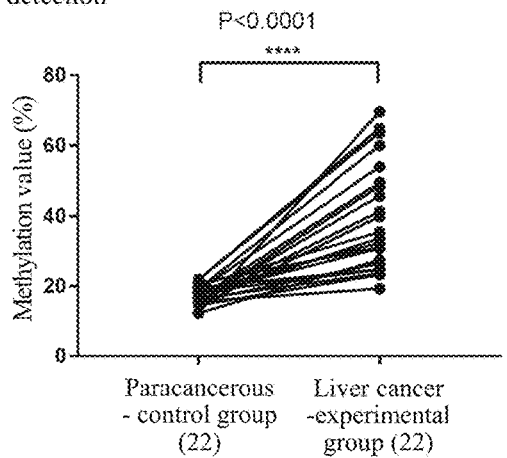
FIG. 5. 10 normal gastric (or gastritis) clinical samples were used as the control group, 10 gastric cancer resection edge clinical samples were used as the experimental group 1, and 20 gastric cancer clinical samples were used as experimental group 2. The STAMP-EP2 methylation value (left), the detection specificity and sensitivity (right) were compared between the control group and the experimental group.
Figure 5:
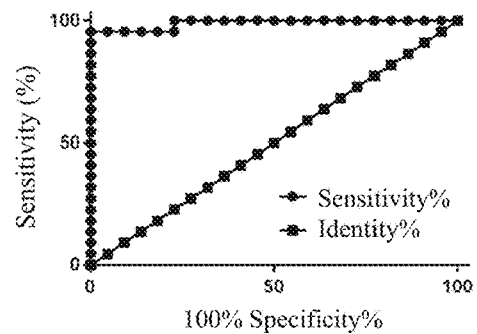

1. Clinical samples: 22 pairs of paracancerous-liver cancer samples were obtained, with paracancerous samples as control group and liver cancer samples as experimental group;
2. Step 2, 3, 4, 5, 6, and 7 are the same as those in Example 2;
8. Results analysis: the methylation value of STAMP-EP2 was compared between the control group and the experimental group, as shown in FIG. 5. It shows that among the clinical samples of liver cancer, the STAMP-EP2 methylation value of the liver cancer experimental group was significantly increased, with P<0.0001, a sensitivity of 100% and a specificity of 100%.

Example 6. STAMP-EP2: Breast Cancer—Clinical Sample Assay—Pyrosequencing

Figure 6:
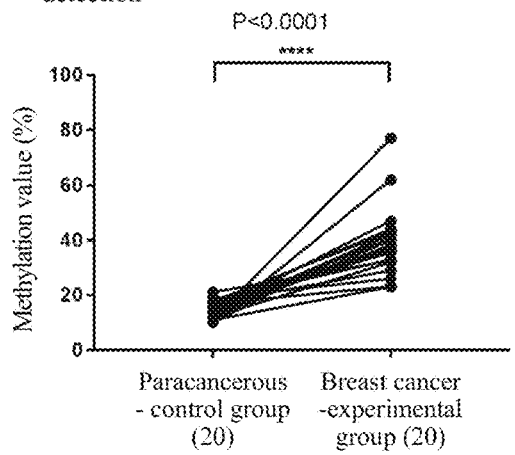
FIG. 6 shows comparison of STAMP-EP2 methylation value (left), the detection specificity and sensitivity (right) between control group and experimental group of 20 pairs of paracancerous-breast cancer samples, with paracancerous samples as control group, and breast cancer samples as experimental group.
Figure 6:
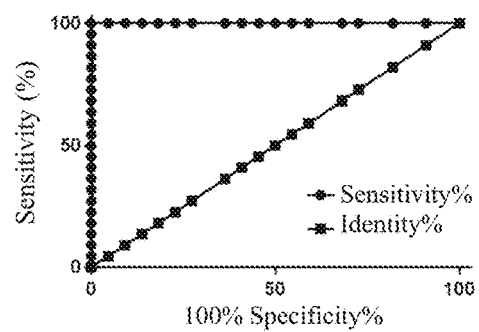

1. Clinical samples: 20 pairs of paracancerous-breast cancer samples were obtained, with paracancerous samples as control group and breast cancer samples as experimental group;
2. Step 2, 3, 4, 5, 6, and 7 are the same as those in Example 2;
8. Results analysis: the methylation value of STAMP-EP2 was compared between the control group and the experimental group, as shown in FIG. 6. It shows that among the clinical samples of breast cancer, the STAMP-EP2 methylation value of the breast cancer experimental group was significantly increased, with P<0.0001, a sensitivity of 100% and a specificity of 100%.

Example 7. STAMP-EP2: Pancreatic Cancer—Clinical Sample Assay—Pyrosequencing

Figure 7:
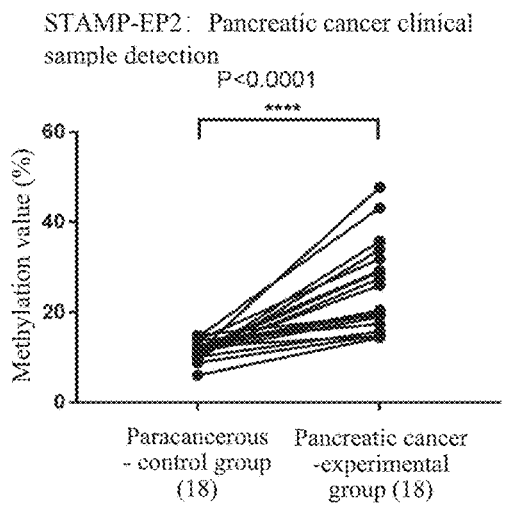
FIG. 7 shows comparison of STAMP-EP2 methylation value (left), the detection specificity and sensitivity (right) between control group and experimental group of 18 pairs of paracancerous-pancreatic cancer samples, with paracancerous samples as control group, and pancreatic cancer samples as experimental group.
Figure 7:
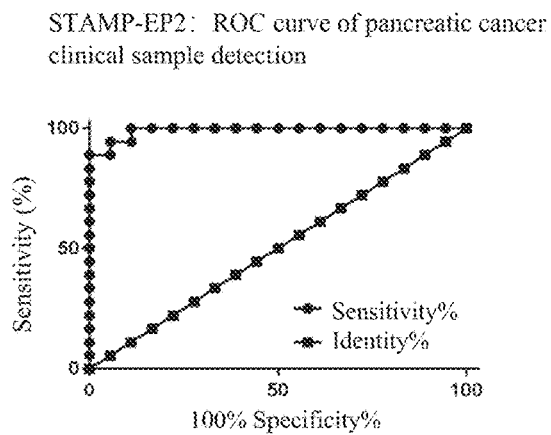

1. Clinical samples: 18 pairs of paracancerous-pancreatic cancer samples were obtained, with paracancerous samples as control group and pancreatic cancer samples as experimental group;
2. Step 2, 3, 4, 5, 6, and 7 are the same as those in Example 2;
8. Results analysis: the methylation value of STAMP-EP2 was compared between the control group and the experimental group, as shown in FIG. 7. It shows that among the clinical samples of pancreatic cancer, the STAMP-EP2 methylation value of the pancreatic cancer experimental group was significantly increased, with P<0.0001, a sensitivity of 88.9% and a specificity of 100%.

Example 8. STAMP-EP2: Head and Neck Cancer—Clinical Sample Assay—Pyrosequencing

Figure 8:
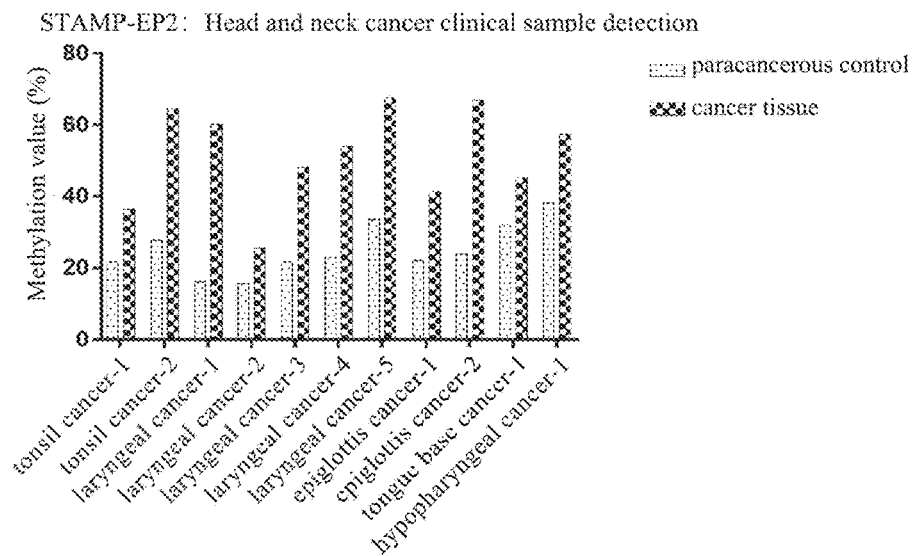
FIG. 8. Eleven pairs of paracancerous-head and neck cancer samples were obtained, including 5 cases of laryngeal cancer, 2 cases of tonsil cancer, 2 cases of epiglottis cancer, 1 case of tongue base cancer, and 1 case of hypopharyngeal cancer. STAMP-EP2 methylation value was compared between control group and experimental group, with paracancerous samples as control group, and cancer samples as experimental group.

1. Clinical samples: 11 pairs of paracancerous-head and neck cancer samples were obtained, including 5 cases of laryngeal cancer, 2 cases of tonsil cancer, 2 cases of epiglottis cancer, 1 case of tongue base cancer, and 1 case of hypopharyngeal cancer. Paracancerous samples were used as control group, and cancer samples as experimental group;
2. Step 2, 3, 4, 5, 6, and 7 are the same as those in Example 2;
8. Results analysis: the methylation value of STAMP-EP2 was compared between the control group and the experimental group, as shown in FIG. 8. It shows that among the clinical samples of head and neck cancer, the STAMP-EP2 methylation value of the head and neck cancer experimental group was significantly increased, with P<0.0001, a sensitivity of 100% and a specificity of 100%.

Example 9. STAMP-EP2: Gallbladder Cancer—Clinical Sample Assay—Pyrosequencing

Figure 9:
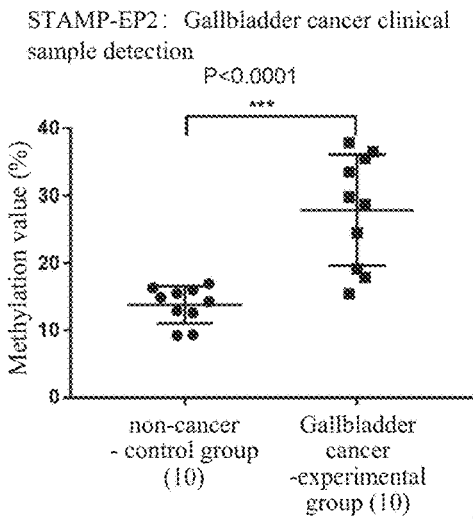
FIG. 9 shows comparison of STAMP-EP2 methylation value (left), the detection specificity and sensitivity (right) between control group and experimental group of bile samples from 10 non-cancer patients and 10 gallbladder cancer patients, with non-cancer samples as control group, and gallbladder cancer samples as experimental group.
Figure 9:
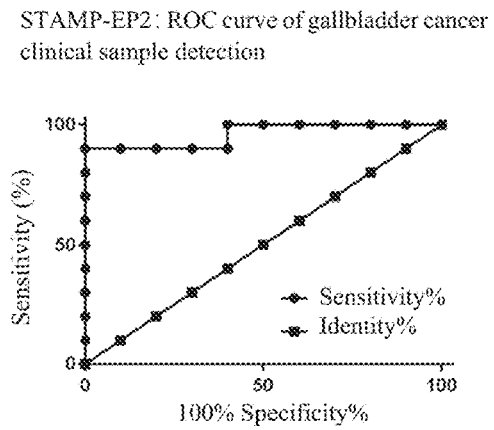

1. Clinical samples: bile samples were obtained from 10 non-cancer patients and 10 gallbladder cancer patients, with non-cancer samples as gallbladder cancer control group and gallbladder cancer samples as gallbladder cancer experimental group;
2. Step 2, 3, 4, 5, 6, and 7 are the same as those in Example 2;
8. Results analysis: the methylation value of STAMP-EP2 was compared between the control group and the experimental group, as shown in FIG. 9. It shows that among the clinical samples of gallbladder cancer, the STAMP-EP2 methylation value of the gallbladder cancer experimental group was significantly increased, with P<0.0001, a sensitivity of 90% and a specificity of 100%.

Example 10. STAMP-EP2: Leukemia—Clinical Sample Assay—Pyrosequencing

Figure 10:
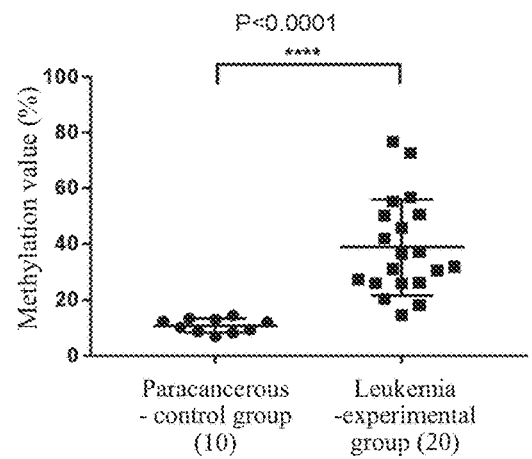
FIG. 10. 10 non-leukemia bone marrow smear samples were used as the control group, and 20 leukemia bone marrow smear samples were used as the experimental group. The STAMP-EP2 methylation value (left), the detection specificity and sensitivity (right) were compared between the leukemia control group and experimental group.
Figure 10:
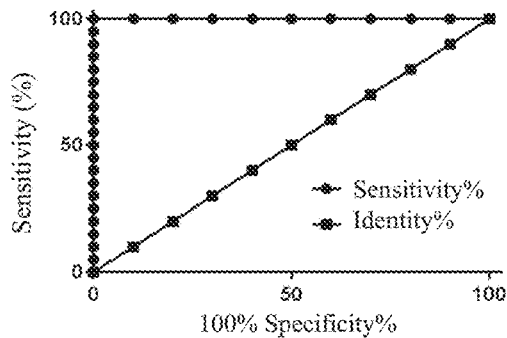

1. Clinical samples: 10 non-leukemia bone marrow smear clinical samples were used as the control group, and 20 leukemia bone marrow smear clinical samples were used as the experimental group;
2. Step 2, 3, 4, 5, 6, and 7 are the same as those in Example 2; 8. Results analysis: the methylation value of STAMP-EP2 was compared between the control group and the experimental group, as shown in FIG. 10. It shows that among the clinical samples of leukemia, the STAMP-EP2 methylation value of the leukemia experimental group was significantly increased, with P<0.0001, a sensitivity of 100% and a specificity of 100%.

Example 11. STAMP-EP2: Renal Cancer—Clinical Sample Assay—Pyrosequencing

Figure 11:
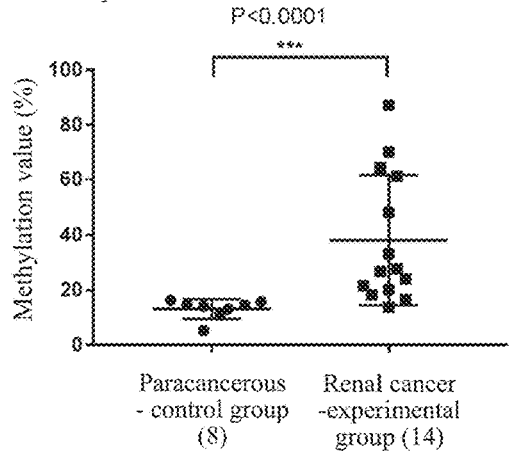
FIG. 11. 8 paracancerous clinical samples of renal cancer were used as the control group, and 14 renal cancer clinical samples were used as the experimental group. The STAMP-EP2 methylation value (left), the detection specificity and sensitivity (right) were compared between the control group and experimental group.
Figure 11:
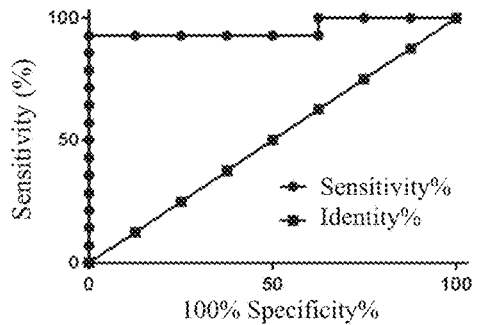

1. Clinical samples: 8 paracancerous clinical samples of renal cancer were used as the control group, and 14 renal cancer clinical samples were used as the experimental group;
2. Step 2, 3, 4, 5, 6, and 7 are the same as those in Example 2;
8. Results analysis: the methylation value of STAMP-EP2 was compared between the control group and the experimental group, as shown in FIG. 11. It shows that among the clinical samples of renal cancer, the STAMP-EP2 methylation value of the renal cancer experimental group was significantly increased, with P<0.0001, a sensitivity of 92.86% and a specificity of 100%.

Example 12. STAMP-EP2: Bladder Cancer—Clinical Sample Assay—Pyrosequencing

Figure 12:
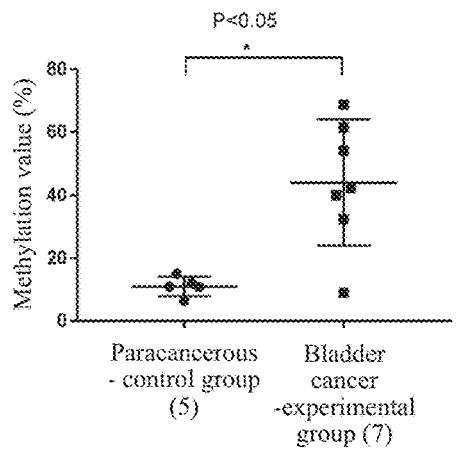
FIG. 12. 5 cases of bladder cancer paracancerous samples and non-cancer urine samples were used as the control group, and 7 cases of bladder cancer tissue samples and bladder cancer urine samples were used as the experimental group. The STAMP-EP2 methylation value was compared between the control group and the experimental group.

1. Clinical samples: 5 cases of bladder cancer paracancerous samples and non-cancer urine samples were used as the control group, and 7 cases of bladder cancer tissue samples and bladder cancer urine samples were used as the experimental group;
2. Step 2, 3, 4, 5, 6, and 7 are the same as those in Example 2;
8. Results analysis: the methylation value of STAMP-EP2 was compared between the control group and the experimental group, as shown in FIG. 12. It shows that among the clinical samples of bladder cancer, the STAMP-EP2 methylation value of the bladder cancer experimental group was significantly increased.

Example 13. STAMP-EP2: Plasma Sample—Clinical Sample Assay

Figure 13:
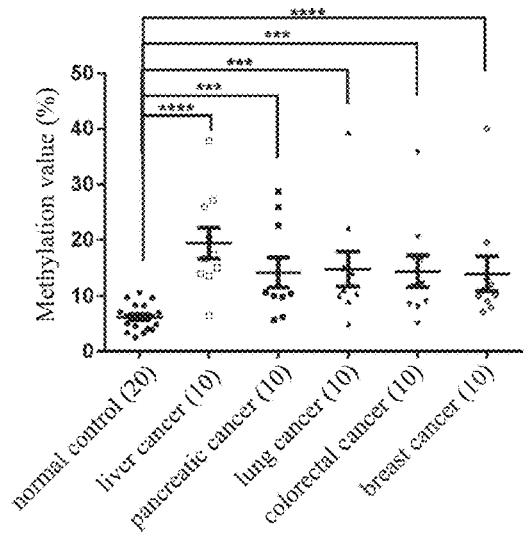
FIG. 13. 20 normal human plasma samples were used as the control group, and plasma samples from patients with different tumor types were obtained, including 10 cases of liver cancer, 10 cases of pancreatic cancer, 10 cases of lung cancer, 10 cases of colorectal cancer and 10 cases of breast cancer. The STAMP-EP2 methylation value was compared between each group.

1. In order to prove that SATMP-C tumor marker can also be detected using liquid biopsy, 20 normal plasma samples were used as the control group, and plasma samples from patients with different tumor types were obtained, including 10 cases of liver cancer, 10 cases of pancreatic cancer, 10 cases of lung cancer, 10 cases of colorectal cancer, and 10 cases of breast cancer;
2. Step 2, 3, 4, 5, 6, and 7 are the same as those in Example 2;
8. Results analysis: as shown in FIG. 13, compared with the normal plasma control group, the STAMP-EP2 methylation values of liver cancer, pancreatic cancer, lung cancer, colorectal cancer and breast cancer groups were significantly increased.

Figure 14:
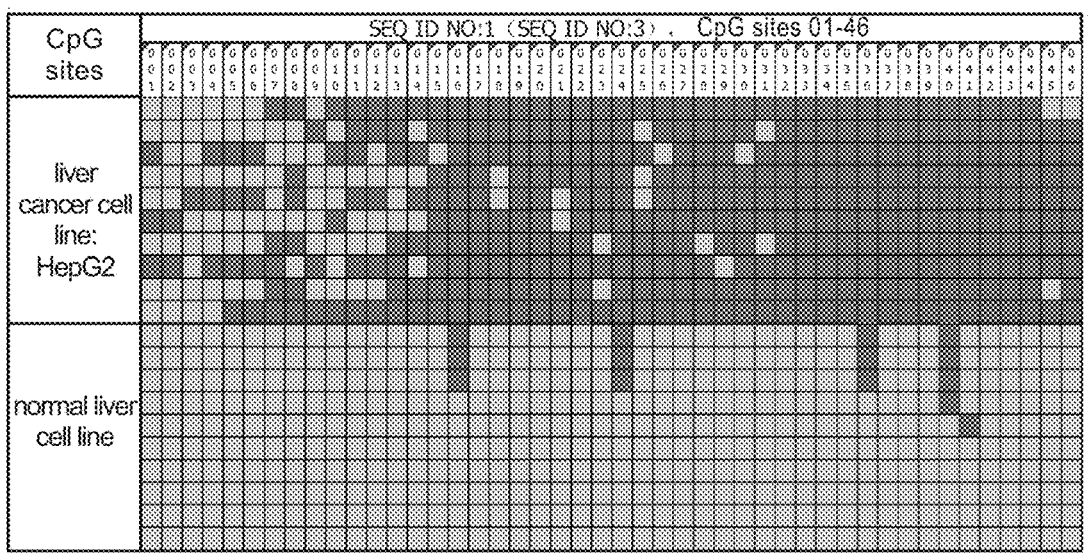
FIG. 14. Methylation difference of CpG site(s) between tumor cell lines and non-tumor cell lines. Dark squares indicate the corresponding sites "methylated", while light squares indicate the corresponding sites "non-methylated".
Figure 14:
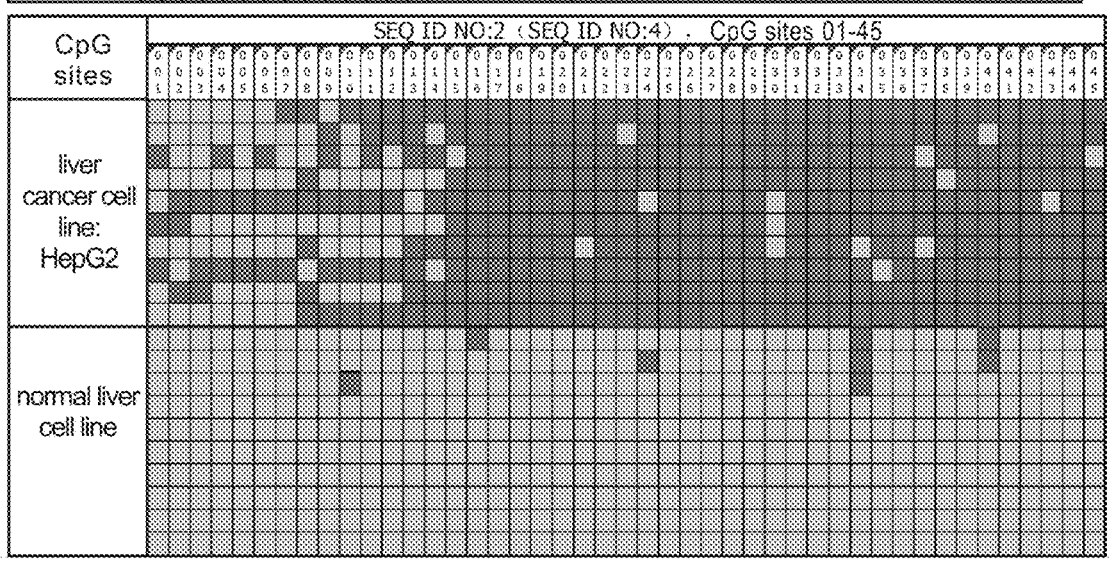

FIG. 14. STAMP-EP2: Methylation Difference of CpG Site(s) Between Tumor Cell Lines and Non-Tumor Cell Lines 1. Genomic DNA was extracted from lung cancer cell line HepG2 and normal lung cell line;
2. The extracted genomic DNA of HepG2 and the normal lung cell line were treated with bisulfite and used as templates for subsequent PCR amplification;
3. Primers were designed according to SEQ ID NO: 1 and 2 by conventional methods for amplification of different sequence regions.
4. After PCR amplification, 2% agarose gel electrophoresis was used to detect the specificity of the PCR fragments. The target fragments were recovered by gel cutting and connected to T vector which was transformed into competent *Escherichia coli*. The bacteria were spread on plate, and clones were selected the next day and sequenced. Ten clones were selected for each fragment for Sanger sequencing.

As shown in FIG. 14, the average methylation value of the SEQ ID NO: 1 region was 3.0% in the normal liver cell line and 78.3% in the liver cancer cell line HepG2. The methylation level of the liver cancer cell line was significantly higher than that of the normal liver cell line. The average methylation value of the SEQ ID NO: 1 region was 1.8% in the normal liver cell line and 78.7% in the liver cancer cell line HepG2. The methylation level of the liver cancer cell line was significantly higher than that of the normal liver cell line.

Each reference provided herein is incorporated by reference to the same extent as if each reference was individually incorporated by reference. In addition, it should be understood that based on the above teaching content of the disclosure, those skilled in the art can practice various changes or modifications to the disclosure, and these equivalent forms also fall within the scope of the appended claims.

I claim:

1. A method for detecting a tumor in a sample comprising: detecting a 5-methylation modification on a CPG site of a polynucleotide using a tumor detection agent or kit, wherein the polynucleotide comprises:
   (a) SEQ ID NO: 1;
   (b) SEQ ID NO: 2;
   (c) a fragment comprising residues 247-305 of SEQ ID NO: 1, or a fragment comprising residues 249-307 of SEQ ID NO: 2; or
   (d) a nucleic acid complementary to the polynucleotide or fragment of (a), (b) or (c);
   wherein the tumor detection agent or kit comprises primers to detect 5-methylation modifications on the CPG sites of a polynucleotide, and
   wherein said primers comprise SEQ ID NO: 9.

2. The method according to claim 1, wherein the tumor is a hematologic tumor; a digestive system tumor; a respiratory system tumor; nervous system tumors; a head and neck tumor; a gynecological and reproductive system tumor; a urinary system tumor; or a skin system tumor.

3. The method according to claim 1, wherein samples of the tumor are tissue samples, paraffin embedded samples, blood samples, pleural effusion samples, and alveolar lavage fluid samples, ascites and lavage fluid samples, bile samples, stool samples, urine samples, saliva samples, sputum samples, cerebrospinal fluid samples, cell smear samples, cervical scraping or brushing samples, or tissue and cell biopsy samples.

4. The method according to claim 1, wherein said method further comprises extracting nucleic acid from said sample.

5. The method according to claim 4, wherein said detecting step comprises:
   (1) treating the extracted nucleic acid to convert an unmodified cytosine into uracil; and
   (2) analyzing the 5-methylation modification in the nucleic acid treated by (1).

6. The method according to claim 2, wherein said hematologic tumor is a leukemia, lymphoma or multiple myeloma; said digestive system tumor is an esophageal-tumor, gastric tumor, colorectal tumor, liver tumor, pancreatic tumor, or bile duct and gallbladder tumor; said respiratory system tumor is a lung tumor or pleuroma; said nervous system tumor is a glioma, neuroblastoma, or meningioma; said head and neck tumor is an oral cancer, tongue cancer, laryngeal tumor or nasopharyngeal tumor; said gynecological and reproductive system tumor is a breast tumor, ovarian tumor, cervical tumor, vulvar tumor, testicular tumor, prostate tumor, or penile tumor; said urinary system tumor is a kidney tumor or bladder tumor; and said skin system tumor is a skin tumor, melanoma, osteosarcoma, liposarcoma or a thyroid tumor.

* * * * *

SEQUENCE LISTING

<160> NUMBER OF SEQ ID NOS: 12

<210> SEQ ID NO 1
<211> LENGTH: 539
<212> TYPE: DNA
<213> ORGANISM: Homo sapiens

<400> SEQUENCE: 1

```
cgccgccgtc ggccagtgca gagcaagcgc tgacgccggg gatccctcag cctctagcct      60
gggattccct gcgcagccaa caacagaaaa gaaaaccagc tcccacacag aggctcccgg     120
ctgcgcagac cttgcccagc acaccagatt gccagctccg agacccggga ctcctcctgt     180 cctggggccga atgctctttt agcgcggtag agtgcacttt ctccaactgg aaaagcgggg    240
acccagcgag aacccgagcg aacgatggga gggagctgcg cgcagaggcg ccgggccggc     300
ccgcggcagg tactatttcc tttgctgctg cctttgttct accccacgct gtgtgagccg     360
atccgctact cgattccgga ggagctggcc aagggctcgg tggtggggaa cctcgctaag     420
gatctagggc ttagtgtcct ggatgtgtcg gctcgcgagc tgcgagtgag cgcggagaag     480
ctgcacttca gcgtagacgc gcagagcggg gacttacttg tgaaggaccg aatagaccg     539
```

<210> SEQ ID NO 2
<211> LENGTH: 541
<212> TYPE: DNA
<213> ORGANISM: Homo sapiens

<400> SEQUENCE: 2

```
cgccgctgtc ggccagtgca gagcaagcgc tgacgccggg gatccgtcag cctctggcct      60
gggattccct gcgcagccaa caacagaaag aagaaaacca gctcccacac agagcctccc    120
ggctgcgcag accttttccca gcacagcgga ttgccagctc cgagacccgg gactcctcct    180
gtcctgggcc gaatgctctt ttagcgcggt agagtgcact ttctccaact ggaaaagcgg    240
ggacccagcg agaacccgag cgaacgatgg gagggagctg cgcgcagagg cgccgggccg    300
gcccgcggca ggtgctattt cctttgctgc tgcctttgtt ctaccccacc ctgagtgagc    360
cgatccgcta ctcgattccg gaggagctgg ccaagggctc ggtggtgggg aacctcgcta    420
aggatctagg gctcagtgtc ctggatgtgt cggctcgcaa gctgcgagtg agcgcggaga    480
agctgcactt cagcgtagac gcggagagcg gggacttact tgtgaagaac cgaatagacc    540
g                                                                    541
```

<210> SEQ ID NO 3
<211> LENGTH: 539
<212> TYPE: DNA
<213> ORGANISM: Artificial Sequence
<220> FEATURE:
<223> OTHER INFORMATION: Bisulfite treated sequence of SEQ ID NO: 1
<220> FEATURE:
<221> NAME/KEY: misc_feature
<222> LOCATION: (1)..(539)
<223> OTHER INFORMATION: Wherein y is either C or U

<400> SEQUENCE: 3

```
yguyguygty gguuagtgua gaguaagygu tgayguyggg gatuuutuag uututaguut      60
gggattuuut gygyaguuaa uaauagaaaa gaaaauuagu tuuuauauag aggutuuygg    120
utgyguagau uttguuuagu auauuagatt guuagutuyg agauuyggga utuutuutgt    180
uutggguyga atgututttt agygyggtag agtguatttt utuuaautgg aaaagygggg    240
auuuagygag aauuygagyg aaygatggga gggagutgyg yguagaggyg uygggutggu    300
uygygguagg tautatttuu tttgutgutg uutttgttut auuuuaygut gtgtgagutyg    360 atuygutaut ygattuygga ggagutgguu aagggutygg tggtgggaa uutygutaag    420 gatutagggu ttagtgtuut ggatgtgtyg gutygyaguu tgygagtgag ygyggagaag    480
utguauttua gygtagaygy guagagyggg gauttauttg tgaaggauyg aatagauyg     539
```

<210> SEQ ID NO 4
<211> LENGTH: 541
<212> TYPE: DNA
<213> ORGANISM: Artificial Sequence
<220> FEATURE:
<223> OTHER INFORMATION: Bisulfite treated sequence of SEQ ID NO: 2
<220> FEATURE:
<221> NAME/KEY: misc_feature
<222> LOCATION: (1)..(541)
<223> OTHER INFORMATION: Wherein y is either C or U

<400> SEQUENCE: 4

```
yguygutgty gguuagtgua gaguaagygu tgayguyggg gatuygtuag uututgguut      60
gggattuuut gyguaguuaa uaauagaaag aagaaaauua gutuuuauau agaguutuuy     120
ggutgyguag auutttuuua guauagygga ttguuagutu ygagauuygg gautuutuut    180
gtuutggguy gaatgututt ttagygyggt agagtguaut ttutuuaaut ggaaaagygg    240
ggauuuagyg agaauuygag ygaaygatgg gagggagutg ygyguagagg yguyggguyg    300
guuygyggua ggtgutattt uutttgutgu tguutttgtt utauuuuauu utgagtgagu    360
ygatuyguta utygattuyg gaggagutgg uuaaggguty ggtggtgggg aauutyguta    420
aggatutagg gutuagtgtu utggatgtgt yggutyguaa gutgygagtg agygyggaga    480
agutguautt uagygtagay gyggagagyg gggauttaut tgtgaagaau ygaatagauy    540
g                                                                    541
```

<210> SEQ ID NO 5
<211> LENGTH: 539
<212> TYPE: DNA
<213> ORGANISM: Homo sapiens

<400> SEQUENCE: 5

```
cggtctattc ggtccttcac aagtaagtcc ccgctctgcg cgtctacgct gaagtgcagc    60
ttctccgcgc tcactcgcag ctcgcgagcc gacacatcca ggacactaag ccctagatcc   120
ttagcgaggt tccccaccac cgagcccttg gccagctcct ccggaatcga gtagcggatc   180
ggctcacaca gcgtggggta gaacaaaggc agcagcaaag gaaatagtac ctgccgcggg   240
ccggcccggc gcctctgcgc gcagctccct cccatcgttc gctcgggttc tcgctgggtc   300
cccgcttttc cagttggaga aagtgcactc taccgcgcta aaagagcatt cggcccagga   360
caggaggagt cccgggtctc ggagctggca atctggtgtg ctgggcaagg tctgcgcagc   420
cgggagcctc tgtgtgggag ctggtttttct tttctgttgt tggctgcgca gggaatccca   480
ggctagaggc tgagggatcc ccggcgtcag cgcttgctct gcactggccg acggcggcg    539
```

<210> SEQ ID NO 6
<211> LENGTH: 541
<212> TYPE: DNA
<213> ORGANISM: Homo sapiens

<400> SEQUENCE: 6

```
cggtctattc ggttcttcac aagtaagtcc ccgctctccg cgtctacgct gaagtgcagc    60
ttctccgcgc tcactcgcag cttgcgagcc gacacatcca ggacactgag ccctagatcc   120
ttagcgaggt tccccaccac cgagcccttg gccagctcct ccggaatcga gtagcggatc   180
ggctcactca gggtggggta gaacaaaggc agcagcaaag gaaatagcac ctgccgcggg   240
ccggcccggc gcctctgcgc gcagctccct cccatcgttc gctcgggttc tcgctgggtc   300
cccgcttttc cagttggaga aagtgcactc taccgcgcta aaagagcatt cggcccagga   360
```

```
caggaggagt cccgggtctc ggagctggca atccgctgtg ctgggaaagg tctgcgcagc    420
cgggaggctc tgtgtgggag ctggtttct tctttctgtt gttggctgcg cagggaatcc     480
caggccagag gctgacggat ccccggcgtc agcgcttgct ctgcactggc cgacagcggc    540
g                                                                    541
```

```
<210> SEQ ID NO 7
<211> LENGTH: 539
<212> TYPE: DNA
<213> ORGANISM: Artificial Sequence
<220> FEATURE:
<223> OTHER INFORMATION: Bisulfite treated sequence of SEQ ID NO: 5
<220> FEATURE:
<221> NAME/KEY: misc_feature
<222> LOCATION: (1)..(539)
<223> OTHER INFORMATION: Wherein y is either C or U

<400> SEQUENCE: 7
yggtutatty ggtuuttuau aagtaagtuu uygututgyg ygtutaygut gaagtguagu     60
ttutuygygu tuautygaug utygygaguy gauauatuua ggauautaag uuutagatuu    120
ttagygaggt tuuuuauuau ygaguuuttg guuagutuut uyggaatyga gtagyggaty    180
ggutuauaua gygtggggta gaauaaaggu aguaguaaag gaaatagtau utguygyggg    240 uyggutuyggy guututgygy guagutuuut uuuatygtty gutygggttu tygutgggtu    300 uuygutttu uagttggaga aagtguautu tauygyguta aaagaguatt yggutuuagga    360 uaggaggagt uuygggtuty ggagutggua atutggtgtg utgggtaagg tutgyguagu    420
ygggaguutu tgtgtgggag utggtttut tttutgttgt tggutgygua gggaatuuua    480
ggutagaggu tgagggatuu uyggygtuag yguttgutut guatgguyg ayggyggyg     539
```

```
<210> SEQ ID NO 8
<211> LENGTH: 541
<212> TYPE: DNA
<213> ORGANISM: Artificial Sequence
<220> FEATURE:
<223> OTHER INFORMATION: Bisulfite treated sequence of SEQ ID NO: 6
<220> FEATURE:
<221> NAME/KEY: misc_feature
<222> LOCATION: (1)..(541)
<223> OTHER INFORMATION: Wherein y is either C or U

<400> SEQUENCE: 8
yggtutatty ggttuttuau aagtaagtuu uygututuyg ygtutaygut gaagtguagu     60
ttutuygygu tuautyguag uttgygaguy gauauatuua ggauautgag uuutagatuu    120
ttagygaggt tuuuuauuau ygaguuuttg guuagutuut uyggaatyga gtagyggaty    180
ggutuautua gggtggggta gaauaaaggu aguaguaaag gaaataguau utguygyggg    240 uyggutuyggy guututgygy guagutuuut uuuatygtty gutygggttu tygutgggtu    300 uuygutttu uagttggaga aagtguautu tauygyguta aaagaguatt yggutuuagga    360 uaggaggagt uuygggtuty ggagutggua atuygutgtg utgggaaagg tutgyguagu    420
ygggaggutu tgtgtgggag utggtttut tutttutgtt gttggutgyg uagggaatuu    480
uagguuagag gutgayggat uuuyggygtu agyguttgut utguatggu ygauagyggy    540 g                                                                    541
```

```
<210> SEQ ID NO 9
<211> LENGTH: 28
<212> TYPE: DNA
```

```
<213> ORGANISM: Artificial Sequence
<220> FEATURE:
<223> OTHER INFORMATION: Primer

<400> SEQUENCE: 9
gaatgttttt ttagygyggt agagtgta                                          28

<210> SEQ ID NO 10
<211> LENGTH: 26
<212> TYPE: DNA
<213> ORGANISM: Artificial Sequence
<220> FEATURE:
<223> OTHER INFORMATION: Primer

<400> SEQUENCE: 10
caacaacaaa aaaaataata cctacc                                            26

<210> SEQ ID NO 11
<211> LENGTH: 23
<212> TYPE: DNA
<213> ORGANISM: Artificial Sequence
<220> FEATURE:
<223> OTHER INFORMATION: Primer

<400> SEQUENCE: 11
ttaattggaa aagygggat tta                                                23

<210> SEQ ID NO 12
<211> LENGTH: 62
<212> TYPE: DNA
<213> ORGANISM: Artificial Sequence
<220> FEATURE:
<223> OTHER INFORMATION: Primer

<400> SEQUENCE: 12
gygagaatty gagygaayga tgggagggag ttgygygtag aggygtyggg tyggttygyg       60
gt                                                                     62
```